US012672830B2

(12) United States Patent
Zhang et al.

(10) Patent No.: US 12,672,830 B2
(45) Date of Patent: Jul. 7, 2026

(54) HEART RATE MONITORING METHOD AND APPARATUS

(71) Applicant: Honor Device Co., Ltd., Shenzhen (CN)

(72) Inventors: Xiaowu Zhang, Beijing (CN); Danhong Li, Beijing (CN); Haoxuan Di, Beijing (CN)

(73) Assignee: HONOR DEVICE CO., LTD., Shenzhen (CN)

( * ) Notice: Subject to any disclaimer, the term of this patent is extended or adjusted under 35 U.S.C. 154(b) by 788 days.

(21) Appl. No.: 18/015,432

(22) PCT Filed: Sep. 8, 2022

(86) PCT No.: PCT/CN2022/117858
§ 371 (c)(1),
(2) Date: Jan. 10, 2023

(87) PCT Pub. No.: WO2023/116062
PCT Pub. Date: Jun. 29, 2023

(65) Prior Publication Data
US 2024/0260906 A1 Aug. 8, 2024

(30) Foreign Application Priority Data
Dec. 23, 2021 (CN) .......................... 202111595435.1

(51) Int. Cl.
*A61B 5/00* (2006.01)
*A61B 5/024* (2006.01)

(52) U.S. Cl.
CPC ........ *A61B 5/7253* (2013.01); *A61B 5/02416* (2013.01); *A61B 5/02438* (2013.01);
(Continued)

(58) Field of Classification Search
CPC .............. A61B 5/7253; A61B 5/02416; A61B 5/02438; A61B 5/681; A61B 5/721;
(Continued)

(56) References Cited

U.S. PATENT DOCUMENTS

| | | | |
|---|---|---|---|
| 5,632,272 A | 5/1997 | Diab et al. | |
| 6,684,090 B2 * | 1/2004 | Ali | ......................... A61B 5/746 |
| | | | 600/323 |

(Continued)

FOREIGN PATENT DOCUMENTS

| | | |
|---|---|---|
| CN | 106214143 A | 12/2016 |
| CN | 107638174 A | 1/2018 |

(Continued)

*Primary Examiner* — Christopher Koharski
*Assistant Examiner* — Helene Bor
(74) *Attorney, Agent, or Firm* — Slater Matsil, LLP

(57) ABSTRACT

Embodiments of this application disclose a heart rate monitoring method and apparatus. A harmonic weight value is calculated according to a PPG signal, the harmonic weight value is then used to determine a confidence of a heart rate, and a heart rate value is output only when the confidence is high. The method includes: determining that a wearer of the electronic device is a living body; obtaining a first PPG signal; determining a first heart rate and a confidence of the first heart rate according to the first PPG signal, where the confidence of the first heart rate is determined by weight coefficients of M harmonic signals; outputting the first heart rate in a case that the confidence of the first heart rate meets a preset confidence condition; and displaying the first heart rate.

19 Claims, 8 Drawing Sheets

(52) U.S. Cl.
CPC .............. *A61B 5/681* (2013.01); *A61B 5/721* (2013.01); *A61B 5/7221* (2013.01); *A61B 5/7239* (2013.01); *A61B 5/725* (2013.01); *A61B 5/7405* (2013.01); *A61B 5/743* (2013.01); *A61B 5/7435* (2013.01); *A61B 2560/0462* (2013.01)

(58) Field of Classification Search
CPC ..... A61B 5/7221; A61B 5/7239; A61B 5/725; A61B 5/7405; A61B 5/743; A61B 5/7435; A61B 2560/0462
See application file for complete search history.

(56)                    References Cited

U.S. PATENT DOCUMENTS

| | | | |
|---|---|---|---|
| 2005/0033128 A1 | 2/2005 | Ali et al. | |
| 2016/0051158 A1* | 2/2016 | Silva ...................... | A61B 5/721 |
| | | | 600/479 |
| 2016/0120476 A1 | 5/2016 | Liu et al. | |
| 2017/0354381 A1 | 12/2017 | Kerman | |
| 2019/0192018 A1 | 6/2019 | Zhang et al. | |
| 2019/0192079 A1* | 6/2019 | Groenendaal ...... | A61B 5/02433 |
| 2020/0237315 A1 | 7/2020 | Mazar et al. | |
| 2021/0186430 A1 | 6/2021 | Chiu | |
| 2022/0008019 A1* | 1/2022 | Jones ................. | A61B 5/02427 |

FOREIGN PATENT DOCUMENTS

| | | |
|---|---|---|
| CN | 105816163 B | 3/2019 |
| CN | 111419219 A | 7/2020 |
| CN | 113017589 A | 6/2021 |
| CN | 113229799 A | 8/2021 |
| EP | 2341446 A1 | 7/2011 |
| JP | 2008167783 A | 7/2008 |

* cited by examiner

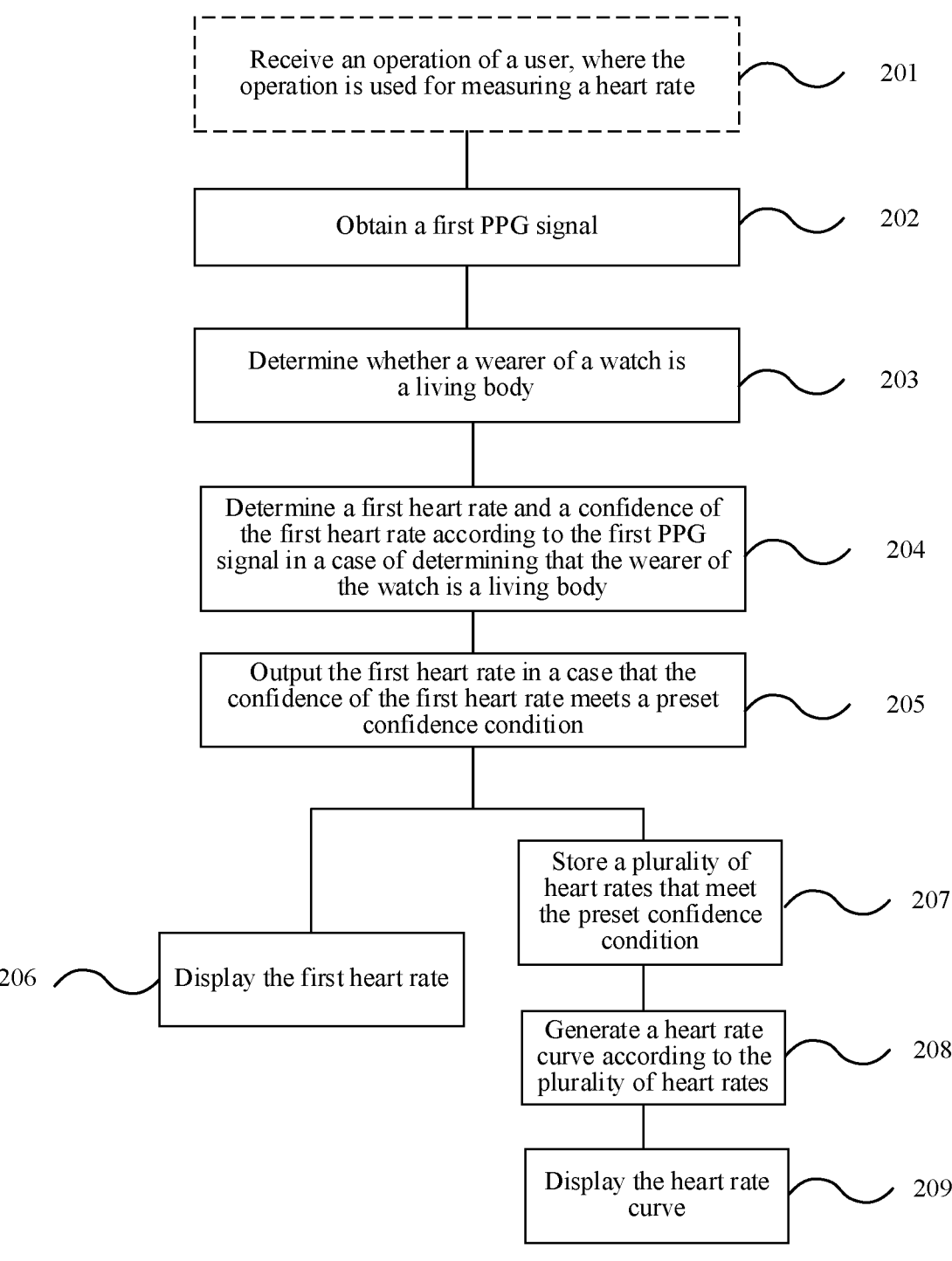

Receive an operation of a user, where the operation is used for measuring a heart rate — 201

Obtain a first PPG signal — 202

Determine whether a wearer of a watch is a living body — 203

Determine a first heart rate and a confidence of the first heart rate according to the first PPG signal in a case of determining that the wearer of the watch is a living body — 204

Output the first heart rate in a case that the confidence of the first heart rate meets a preset confidence condition — 205

206 — Display the first heart rate

Store a plurality of heart rates that meet the preset confidence condition — 207

Generate a heart rate curve according to the plurality of heart rates — 208

Display the heart rate curve — 209

FIG. 2

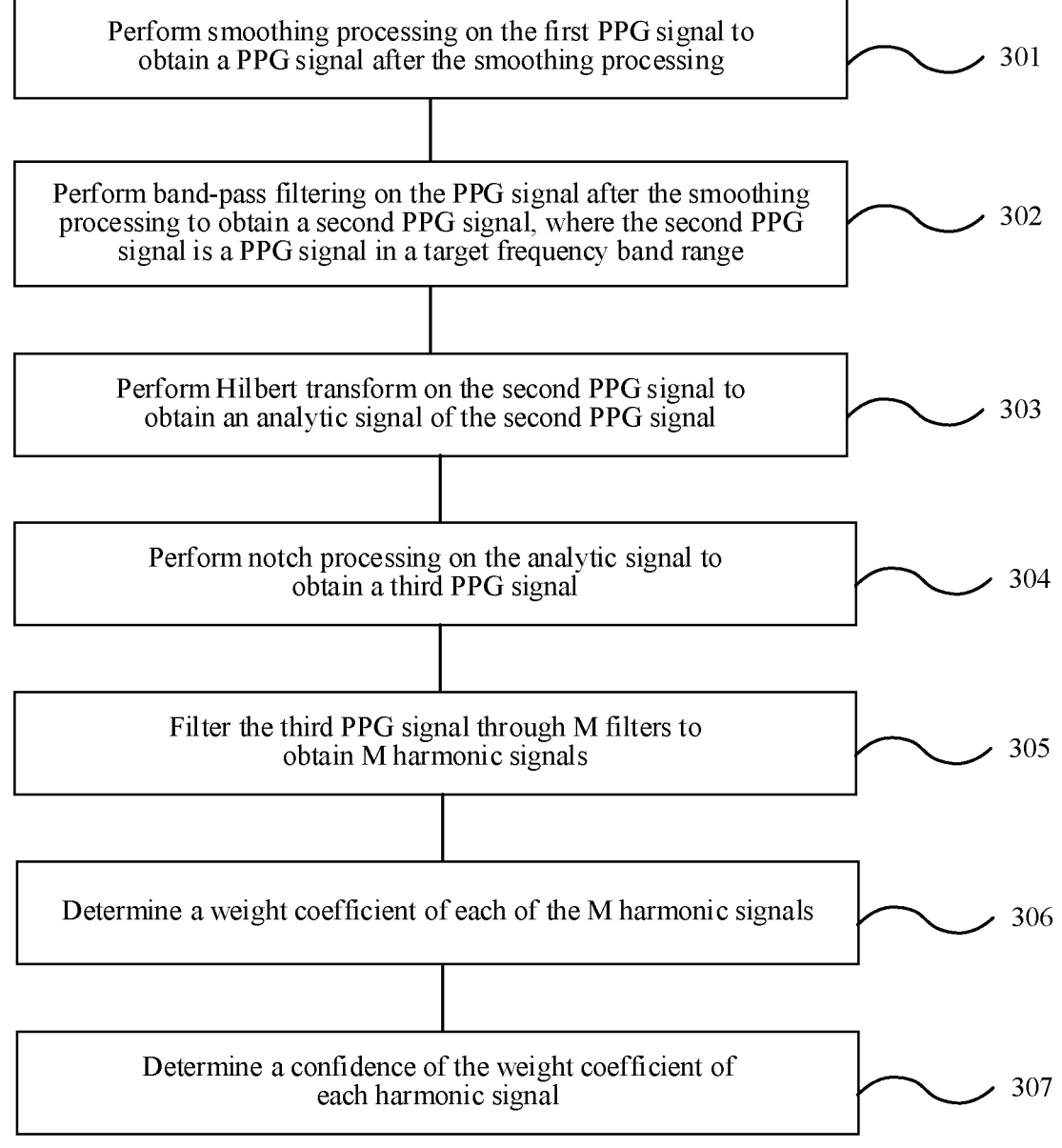

Perform smoothing processing on the first PPG signal to obtain a PPG signal after the smoothing processing          301

Perform band-pass filtering on the PPG signal after the smoothing processing to obtain a second PPG signal, where the second PPG signal is a PPG signal in a target frequency band range          302

Perform Hilbert transform on the second PPG signal to obtain an analytic signal of the second PPG signal          303

Perform notch processing on the analytic signal to obtain a third PPG signal          304

Filter the third PPG signal through M filters to obtain M harmonic signals          305

Determine a weight coefficient of each of the M harmonic signals          306

Determine a confidence of the weight coefficient of each harmonic signal          307

FIG. 3

Apparatus 500

HEART RATE MONITORING METHOD AND APPARATUS

CROSS-REFERENCE TO RELATED APPLICATIONS

This application is a national stage of International Application No. PCT/CN2022/117858, filed on Sep. 8, 2022, which claims priority to Chinese Patent Application No. 202111595435.1, filed on Dec. 23, 2021. The disclosures of both of the aforementioned applications are hereby incorporated by reference in their entireties.

TECHNICAL FIELD

This application relates to the field of terminal technologies, and specifically, to a heart rate monitoring method and apparatus.

BACKGROUND

With the increasing development of functions of a smart watch, the functions of the smart watch are increasing, such as an exercise function and a health monitoring function. Heart rate is an important physiological index of human health conditions. A user can monitor the heart rate through the smart watch. At present, measurement of the heart rate is generally implemented by a photoplethysmograph (photoplethysmograph, PPG) technology.

However, in an actual application, factors such as a position where the user wears the smart watch, tightness of wearing of the smart watch, and skin color of the user affect the quality of a PPG signal. If the user wears the smart watch loosely, the PPG signal is poor, and it is difficult to calculate an accurate heart rate. Accordingly, the user finds that the heart rate is inaccurate, which affects the user experience.

SUMMARY

In view of the above, this application provides a heart rate monitoring method and apparatus, a computer-readable storage medium, and a computer program product, which can provide a user with an accurate heart rate and greatly improve the user experience.

According to a first aspect, a heart rate monitoring method is provided. The method is applied to an electronic device, and includes:

determining that a wearer of the electronic device is a living body;

obtaining a first photoplethysmograph PPG signal;

determining a first heart rate and a confidence of the first heart rate according to the first PPG signal, where the confidence of the first heart rate is determined by weight coefficients of M harmonic signals, where the M harmonic signals are determined according to the first PPG signal within a preset time, and M is an integer greater than or equal to 2;

outputting the first heart rate in a case that the confidence of the first heart rate meets a preset confidence condition; and displaying the first heart rate.

In an embodiment of this application, the first heart rate and the confidence of the first heart rate are determined based on the first PPG signal, and the first heart rate is output in a case that the confidence of the first heart rate meets the preset confidence condition. For example, the first heart rate value is output only in a case that the confidence of the first heart rate is higher than a confidence threshold. In this way, it can be ensured that the output heart rate value has relatively high reliability, a user can know his heart rate in real time, and the user can be provided with a heart rate having relatively high accuracy.

In a possible implementation, a second heart rate is displayed in a case that the confidence of the first heart rate does not meet the preset confidence condition, where the second heart rate is a heart rate that meets the preset confidence condition last time. In this way, even though the confidence of the first heart rate does not meet the preset confidence condition, a heart rate that meets the preset confidence condition last time can be displayed, thereby ensuring that the heart rate value presented to the user has relatively high reliability.

In a possible implementation, that the confidence of the first heart rate meets a preset confidence condition includes: the confidence of the first heart rate is greater than a confidence threshold.

In a possible implementation, the method further includes:

calculating a weight coefficient of each of the M harmonic signals;

determining a confidence of the weight coefficient of each harmonic signal to obtain M confidences; and using a highest confidence among the M confidences as the confidence of the first heart rate.

That is, after the M confidences are obtained based on the M harmonic signals, the highest confidence may be selected as the confidence of the first heart rate, to accurately reflect the heart rate of the user.

In a possible implementation, the calculating a weight coefficient of each of the M harmonic signals includes:

calculating a relative error of each harmonic signal relative to an ideal signal, where the ideal signal refers to a signal obtained by multiplying a signal at a previous moment of a current moment by a phase at a next moment; and dividing the relative error of each harmonic signal by a sum of relative errors of the M harmonic signals to obtain the weight coefficient of each harmonic signal.

Based on the foregoing manner, the weight coefficient of each harmonic signal can be obtained to provide a basis for determining the confidence of the weight coefficient of each harmonic signal.

In a possible implementation, the method further includes:

performing smoothing processing on the first PPG signal to obtain a PPG signal after the smoothing processing;

performing band-pass filtering on the PPG signal after the smoothing processing to obtain a second PPG signal, where the second PPG signal is a PPG signal in a target frequency band range;

performing Hilbert transform on the second PPG signal to obtain an analytic signal of the second PPG signal, where a derivative of a phase of the analytic signal is an instantaneous frequency;

performing notch processing on the analytic signal to obtain a third PPG signal, where the third PPG signal does not include a motion interference signal; and filtering the third PPG signal through M filters to obtain the M harmonic signals.

In general, the PPG signal acquired by a heart rate sensor further includes interference from an ACC signal. Using an application scenario as an example for description, when the user wears a watch, in addition to pulse motion, an arm of the user may also move, so that the PPG signal acquired by the heart rate sensor also includes a signal generated by arm motion. The signal generated by the arm motion of the user is generally acquired by an acceleration sensor ACC. Herein, by notch processing, an impact of the arm motion on the PPG signal can be eliminated, that is, the interference from the ACC signal is eliminated, thereby obtaining a more accurate PPG signal.

In a possible implementation, the performing smoothing processing on the first PPG signal to obtain a PPG signal after the smoothing processing includes:

calculating, in a case that a signal abnormality of a current frame is identified, a sum of data of a previous frame of the current frame and data of a next frame of the current frame, and calculating an average value based on the sum of the data of the previous frame of the current frame and the data of the next frame of the current frame; and using the average value as a value of the current frame after the smoothing processing.

An inaccurate signal can be removed through the foregoing smoothing processing manner. The inaccurate signal includes cases of an excessively large signal or excessively small signal. For example, the inaccurate signal is caused by excessively loose wearing.

In a possible implementation, the determining a confidence of the weight coefficient of each harmonic signal includes:

determining the confidence corresponding to the weight coefficient of each harmonic signal according to a confidence interval threshold, where the confidence interval threshold is determined by big data sample statistics.

Herein, the confidence interval threshold is obtained by using the method of big data sample statistics, so that there is good generalization performance for a plurality of scenarios.

In a possible implementation, the method further includes:

storing a plurality of heart rate values whose confidences meet the preset confidence condition;

generating a heart rate curve based on the plurality of heart rate values; and displaying the heart rate curve.

The heart rate curve generated based on heart rates with a high confidence can accurately reflect a heart rate change of the user within a certain period of time, helping to improve the user experience.

According to a second aspect, a heart rate monitoring apparatus is provided, including units configured to perform any method according to the first aspect. The apparatus may be a watch (or a smart watch), or a chip in a watch (or a smart watch). The apparatus includes an input unit, a display unit, and a processing unit.

In a case that the apparatus is a watch, the processing unit may be a processor, the input unit may be a communication interface, and the display unit may be a graphic processing module and screen. The watch may further include a memory, configured to store computer program code, where the computer program code stored in the memory, when executed by the processor, causes the terminal to perform any method of according to the first aspect.

In a case that the apparatus is a chip in a watch, the processing unit may be a logic processing unit in the chip, the input unit may be an output interface, a pin, a circuit, or the like, and the display unit may be a graphic processing unit in the chip. The chip may further include a memory, and the memory may be a memory (for example, a register or a cache) in the chip, or a memory (for example, a read-only memory or a random access memory) located outside the chip. The memory is configured to store computer program code, where the computer program code stored in the memory, when executed by the processor, causes the chip to perform any method according to the first aspect.

Optionally, in a possible implementation, the input unit is configured to receive an operation of the user, where the operation is used for measuring a heart rate.

The processing unit is configured to determine that a wearer of an electronic device is a living body;

further configured to obtain a first PPG signal;

further configured to determine a first heart rate and a confidence of the first heart rate according to the first PPG signal, where the confidence of the first heart rate is determined by weight coefficients of M harmonic signals, where the M harmonic signals are determined according to the first PPG signal within a preset time, and M is an integer greater than or equal to 2;

and further configured to output the first heart rate in a case that the confidence of the first heart rate meets a preset confidence condition.

The display unit is configured to display the first heart rate.

In a possible implementation, the display unit is configured to display a second heart rate in a case that the confidence of the first heart rate does not meet the preset confidence condition, where the second heart rate is a heart rate that meets the preset confidence condition last time.

In a possible implementation, the processing unit is further configured to:

calculate a weight coefficient of each of the M harmonic signals;

determine a confidence of the weight coefficient of each harmonic signal to obtain M confidences; and use a highest confidence among the M confidences as the confidence of the first heart rate.

In a possible implementation, that the processing unit is configured to determine a confidence of the weight coefficient of each harmonic signal specifically includes:

determining the confidence corresponding to the weight coefficient of each harmonic signal according to a confidence interval threshold, where the confidence interval threshold is determined by big data sample statistics.

In a possible implementation, that the processing unit is configured to calculate a weight coefficient of each of the M harmonic signals specifically includes:

calculating a relative error of each harmonic signal relative to an ideal signal, where the ideal signal refers to a signal obtained by multiplying a signal at a previous moment of a current moment by a phase at a next moment; and dividing the relative error of each harmonic signal by a sum of relative errors of the M harmonic signals to obtain the weight coefficient of each harmonic signal.

In a possible implementation, the processing unit is further configured to:

perform smoothing processing on the first PPG signal to obtain a PPG signal after the smoothing processing;

perform band-pass filtering on the PPG signal after the smoothing processing to obtain a second PPG signal, where the second PPG signal is a PPG signal in a target frequency band range;

perform Hilbert transform on the second PPG signal to obtain an analytic signal of the second PPG signal, where a derivative of a phase of the analytic signal is an instantaneous frequency;

perform notch processing on the analytic signal to obtain a third PPG signal, where the third PPG signal does not include a motion interference signal; and filter the third PPG signal through M filters to obtain the M harmonic signals.

In a possible implementation, that the processing unit is configured to perform smoothing processing on the first PPG signal to obtain a PPG signal after the smoothing processing specifically includes:

calculating a sum of data of a previous frame of the current frame and data of a next frame of the current frame, and calculating an average value based on the sum of the data of the previous frame of the current frame and the data of the next frame of the current frame; and using the average value as a value of the current frame after the smoothing processing.

Optionally, that the confidence of the first heart rate meets a preset confidence condition includes:

the confidence of the first heart rate is greater than a confidence threshold.

In a possible implementation, the processing unit is further configured to:

store a plurality of heart rate values whose confidences meet the preset confidence condition; and generate a heart rate curve based on the plurality of heart rate values.

The display unit is configured to display the heart rate curve.

According to a third aspect, a computer-readable storage medium is provided, storing computer program code, where the computer program code, when run by a heart rate monitoring apparatus, causes the apparatus to perform any method according to the first aspect.

According to a fourth aspect, a computer program product is provided, including computer program code, where the computer program code, when run by a heart rate monitoring apparatus, causes the apparatus to perform any method according to the first aspect.

BRIEF DESCRIPTION OF THE DRAWINGS

FIG. 2 is a schematic flowchart of a heart rate monitoring method according to an embodiment of this application;

FIG. 3 is a schematic flowchart of a method for determining a heart rate confidence according to an embodiment of this application;

DETAILED DESCRIPTION OF ILLUSTRATIVE EMBODIMENTS

The following describes technical solutions in embodiments of this application with reference to the accompanying drawings.

The embodiments of this application are applicable to an electronic device, where the electronic device may be a smart watch, a wristband, or another wearable device that can be configured to monitor a heart rate. In the embodiments of this application, a smart watch is used as an example for description. At present, the smart watch measures a pulse or a heart rate of a user by a photoplethysmograph (photoplethysmograph, PPG) technology.

The principle of measuring a pulse or a heart rate by the PPG technology is as follows: Light of a specific color and wavelength is emitted into a human body through a light-emitting diode (light-emitting diode, LED), then attenuated light reflected and absorbed by human blood vessels and tissues is measured, and a pulse state of the blood vessels is traced, to thereby achieve the purpose of detecting a pulse signal.

For example, a heart rate sensor (for example, a PPG sensor or a PPG module) may be arranged in the smart watch. The smart watch acquires a PPG signal through the heart rate sensor and obtains an instantaneous heart rate of the user based on the PPG signal. The type of the heart rate sensor is not specifically limited in the embodiments of this application. For example, the heart rate sensor includes a reflective photoelectric heart rate sensor, a transmissive photoelectric heart rate sensor, and the like.

However, factors such as a wearing state and tightness of the smart watch affect the quality of the PPG signal and finally affect the reliability of a heart rate output value, thereby affecting the user experience. The following description is made with reference to a scenario in FIG. 1 as an example.

Figure 1:
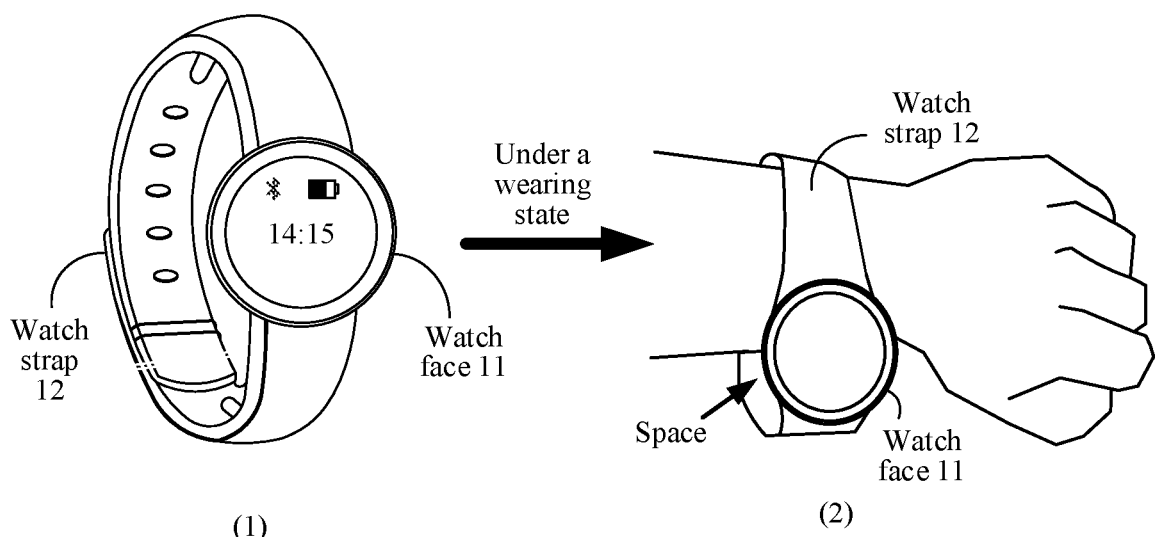
FIG. 1 is an exemplary diagram of an application scenario according to an embodiment of this application.

A smart watch is shown in (1) in FIG. 1, including a watch face 11 and a watch strap 12. A user can wear the smart watch on a wrist through the watch strap 12, so that the back of the watch face 11 can cling to skin. The user can adjust tightness of wearing by adjusting the watch strap 12. If the watch strap 12 is adjusted to be relatively loose, a state of the user wearing the smart watch may be shown in (2) in FIG. 1. It can be learned from (2) in FIG. 1 that the user adjusts the watch strap 12 to be relatively loose, resulting in certain space between the watch face 11 and an arm. The back of the watch face 11 of the smart watch does not completely cling to the wrist. If the smart watch is worn excessively loosely, the smart watch may be caused to move or flip over the wrist of the user, which further results in an inaccurate heart rate measured by the heart rate sensor.

In the scenario shown in (2) in FIG. 1, the heart rate measured by the smart watch may be inaccurate, that is, the heart rate may fluctuate greatly. That the heart rate fluctuates greatly includes: the heart rate is excessively high or is excessively low. For example, if a heart rate measured at the first second is 80, a heart rate measured at the second second is 81, a heart rate measured at the third second is 120, a heart rate measured at the fourth second is 80, and a heart rate measured at the fifth second is 81, the heart rate at the third second is excessively high. In another example, if a heart rate measured at the first second is 80, a heart rate measured at the second second is 81, a heart rate measured at the third second is 20, a heart rate measured at the fourth second is 80, and a heart rate measured at the fifth second is 81, the heart rate at the third second is excessively low.

It should be understood that FIG. 1 only schematically describes an application scenario of this application, which does not constitute a limitation on this embodiment of this application, and this application is not limited thereto. For example, the smart watch may move to a bone knuckle. In another example, as the arm swings, the smart watch swings back and forth with the arm. Technical solutions of this embodiment of this application are applicable to all these scenarios.

In view of this, an embodiment of this application provides a heart rate monitoring method and an electronic device. In the heart rate monitoring method of this embodiment of this application, a harmonic weight coefficient (or harmonic weight value) is calculated based on a PPG signal, and the harmonic weight coefficient is then used to determine a corresponding confidence, and a heart rate value is output only when the confidence of the heart rate is high, so that the accuracy of the heart rate output value can be ensured, and the user experience can be improved.

The heart rate monitoring method of this embodiment of this application is described below with reference to a procedure in FIG. 2. For ease of description, the smart watch is referred to as the "watch" for short. FIG. 2 is a schematic flowchart of a heart rate monitoring method according to an embodiment of this application. As shown in FIG. 2, the heart rate monitoring method includes:

Step 201. Receive an operation of a user, where the operation is used for measuring a heart rate. Alternatively, the operation is used for triggering a heart rate monitoring function.

This embodiment of this application does not limit a specific manner of the operation. For example, the operation may be that the user clicks on an application (for example, motion monitoring or single measurement in a UI interface) in the UI interface to trigger the heart rate monitoring function.

The application can receive the operation of the user. The application includes the heart rate monitoring function. For example, the application includes, but is not limited to, applications such as heart rate, exercise recording, exercise, and health monitoring.

In a possible example, after receiving the operation of the user, the application may send a trigger action to a system, so that the system invokes a heart rate sensor to acquire data (such as a PPG signal).

It should be noted that, step 201 is an optional step. In other words, step 201 is a possible implementation of triggering the watch to measure the heart rate, that is, the watch may start heart rate measurement after receiving the operation of the user (which may alternatively be understood as that the watch passively measures the heart rate), but this application is not limited thereto. In fact, the watch may alternatively actively measure the heart rate. For example, in a scenario that the user wears the watch, the watch can display a reading of the heart rate value of the user at any time, so that the user can raise the wrist at any time to know a real-time heart rate of the user rate.

Step 202. Obtain a first PPG signal.

It may be understood that the watch can obtain the first PPG signal regardless of whether the watch measures the heart rate actively or passively.

Specifically, the obtaining a first PPG signal includes: acquiring the first PPG signal through the heart rate sensor.

As a possible implementation, after obtaining a heart rate monitoring action triggered by an application, the system can invoke the heart rate sensor (for example, a PPG sensor or a PPG module) to acquire the PPG signal.

In this embodiment of this application, a heart rate calculation can be performed based on the acquired PPG signal. Before the heart rate is calculated, optionally, whether the watch is in a wearing state can be detected first, in other words, whether the watch is worn by the user can be detected first.

Step 203. Determine whether a wearer of the watch is a living body.

It should be understood that whether the wearer of the watch is a living body is determined to detect whether the watch is worn by the user herein. In a case that the user wears the watch, there is a need for heart rate monitoring.

As a possible implementation, whether the wearer of the watch is a living body can be detected in combination with an infrared detection technology and a living body wearing algorithm.

Optionally, the detecting whether a wearer of the watch is a living body can be implemented by the following steps:

Step 1. Determine whether the watch is worn through infrared detection.

The principle of the infrared detection technology is as follows: Infrared light is incident on an object to be detected and reflected energy is tested; and whether the watch is worn can be determined by comparing the reflected energy with an energy threshold. In general, the amount of reflected energy is different between detection on air and detection on a human hand. If detection is performed on air, less energy is reflected; and if the watch is worn on the human hand, more energy is reflected.

For example, if it is tested that the reflected energy exceeds the energy threshold, it is considered that the watch is worn on the human hand; and if it is tested that the reflected energy is less than the energy threshold, it is considered that the watch is not worn.

Step 2. Determine whether the wearer is a living body through the living body wearing algorithm.

The living body wearing algorithm is implemented based on a living body detection model. Since reflectivity of light after being reflected by a human body is different from that of light after being reflected by a non-human body, it is required to perform training and distinction through the living body detection model. The living body detection model is a trained model that can be configured to distinguish entities wearing the watch. For example, reflectivity of the watch worn on the human hand is different from that of the watch worn on a cup. Whether the watch is worn on the human body can be learned based on the living body detection model.

Optionally, after whether the wearer of the electronic device is a living body is detected through the foregoing steps, a wearing result can be returned to the system. The wearing result is used to indicate whether the wearer of the watch is a living body (or whether the user wears the watch).

Optionally, in a possible implementation, the wearing result may be identified through an identification value. For example, if the identification value is 0, it indicates that the watch is detected not to be worn by the user; and if the identification value is 1, it indicates that the watch is detected to be in a wearing state.

In a case in which the watch is detected to be worn by the user, step 202 can be performed. For example, the first PPG signal is acquired through the heart rate sensor to calculate the heart rate of the user.

It should be understood that an order of performing step 202 and step 203 is not limited in this embodiment of this application. The two steps may be performed simultaneously; or step 202 may be performed first and then step 203 is performed; or step 203 may be performed first and then step 202 is performed.

Step 204. Determine a first heart rate and a confidence of the first heart rate according to the first PPG signal in a case of determining that the wearer of the watch is a living body.

The confidence of the heart rate is used to represent the reliability of the heart rate value. For example, when the confidence of the heart rate is higher, it indicates that the reliability of the heart rate value is higher; and when the confidence of the heart rate is lower, it indicates that the reliability of the heart rate value is lower.

In this embodiment of this application, the confidence of the heart rate can also be calculated while the heart rate is calculated. The confidence of the heart rate is obtained by calculating a harmonic weight value of the PPG signal. Step 204 is described in detail below with reference to FIG. 3.

Step 205. Output the first heart rate in a case that the confidence of the first heart rate meets a preset confidence condition. In other words, output the first heart rate (for example, the first heart rate is a heart rate with a high confidence) according to a confidence output strategy. The heart rate with a high confidence refers to a heart rate whose confidence meets a confidence threshold. For example, the heart rate with a high confidence refers to the heart rate whose confidence is greater than a confidence threshold. For ease of description, the heart rate with a high confidence is used as an example for description.

The confidence output strategy refers to: determining whether to output the heart rate value based on the value of the confidence of the heart rate. For example, if the confidence of the heart rate is relatively high, it indicates that the heart rate value is relatively reliable, and the heart rate value can be output; and if the confidence of the heart rate is relatively low, it indicates that the heart rate value is unreliable, and the heart rate value can be discarded.

In this embodiment of this application, the confidence level can be determined by setting the confidence threshold, so as to determine whether the heart rate is output. Optionally, as a possible implementation, the confidence output strategy refers to: that when the confidence of the heart rate is greater than the confidence threshold, it is considered that the heart rate is a heart rate with a high confidence, and the heart rate can be output in this case; and when the confidence of the heart rate is less than or equal to the confidence threshold, it is considered that the heart rate is a heart rate with a low confidence, and the heart rate is not output in this case. The heart rate with a high confidence refers to a heart rate whose confidence is greater than the confidence threshold.

In some possible embodiments, after the heart rate with a high confidence is obtained, the heart rate value with a high confidence may be returned to the application, so that the heart rate value may subsequently be presented to the user in real time through an interface.

In other words, step 205 may alternatively be replaced with outputting the first heart rate in a case that the confidence of the first heart rate meets the preset confidence condition. It should be understood that the foregoing heart rate with a high confidence may be considered as an exemplary description of the heart rate that meets the preset confidence condition.

In some possible embodiments, that the confidence of the first heart rate meets the preset confidence condition includes: the confidence of the first heart rate is greater than the confidence threshold. For example, if the confidence of the first heart rate is 1, and the confidence threshold is 2, it can be learned that the confidence of the first heart rate is less than the confidence threshold. In this case, the heart rate is not output. If the confidence of the first heart rate is 2, and the confidence threshold is 1, it can be determined that the confidence of the first heart rate is greater than the confidence threshold. In this case, the heart rate is output.

Alternatively, in some possible embodiments, that the confidence of the first heart rate meets the preset confidence condition includes: the confidence of the first heart rate falls into a high confidence interval.

Step 206. Display the first heart rate. In other words, display the heart rate that meets the preset confidence condition.

For example, in an exercise scenario, the user raises the wrist to know a real-time exercise heart rate of the user. The heart rate with a high confidence is displayed on the UI interface, which allows the user to know the heart rate of the user in real time, and can provide the user with a relatively accurate heart rate.

Optionally, step 207, store heart rates with a high confidence. In other words, store a plurality of heart rate values that meet the preset confidence condition.

After the heart rate values with a high confidence are obtained, the heart rate values with a high confidence can be saved or stored for subsequent use in generating a heart rate curve.

A case in which the first heart rate is output and displayed when the confidence of the first heart rate meets the preset confidence condition is described above. It should be noted that, a second heart rate is displayed in a case that the confidence of the first heart rate does not meet the preset confidence condition, where the second heart rate is a heart rate that meets the preset confidence condition last time. A confidence of the second heart rate meets the preset confidence preset condition. It may be understood that, the confidence of the second heart rate can be determined through the heart rate monitoring method of this embodiment of this application.

For example, it is assumed that a heart rate at the first second is 80, a heart rate at the second second is 81, a heart rate at the third second is 90, a heart rate at the fourth second is 80, and a heart rate at the fifth second is 81. A confidence of the heart rate at the third second can be calculated through the heart rate monitoring method of this embodiment of this application. When it is determined that the confidence of the heart rate at the third second does not meet the preset confidence condition, the heart rate is not output, that is, 90 is not displayed at the third second, and a heart rate value at the second second is still used (or continue) to be displayed. That is, the heart rate at the first second is 80, the heart rate at the second second is 81, the heart rate at the third second is 81, the heart rate at the fourth second is 80, and the heart rate at the fifth second is 81. A confidence of the heart rate at the second second meets the preset confidence condition. It may be understood that the confidence of heart rate at the second second may alternatively be determined by the heart rate monitoring method of this embodiment of this application.

It may further be understood that the foregoing examples are merely for ease of understanding, but this application is not limited thereto.

Optionally, step 208, generate a heart rate curve according to heart rates with a high confidence.

As a possible implementation, after the plurality of heart rate values with a high confidence are obtained, the heart rate curve can be generated based on the plurality of heart rate values with a high confidence. The heart rate curve generated based on the heart rates with a high confidence can accurately reflect a heart rate change of the user within a certain period of time, helping to improve the user experience.

For example, it is assumed that the heart rate at the first second is 80, the heart rate at the second second is 81, the heart rate at the third second is 90, the heart rate at the fourth second is 80, and the heart rate at the fifth second is 81. When it is determined that the confidence of the heart rate at the third second does not meet the preset confidence condition, the heart rate curve from the first second to the fifth second is drawn without using the heart rate value at the third second, but the following heart rate values are used for drawing the curve: the heart rate value 80 at the first second, the heart rate value 81 at the second second, the heart rate value 80 at the fourth second, and the heart rate value 81 at the fifth second. The confidences of the heart rates used to draw the heart rate curve meets the preset confidence condition.

Optionally, step 209, display the heart rate curve.

For example, after the exercise ends, the user views a change trend of heart rates during the exercise. The heart rate curve generated based on the heart rate values with a high confidence is displayed on the UI interface, which allows the user to view a relatively accurate change trend of the heart rates.

In this embodiment of this application, the first heart rate and the confidence of the first heart rate are determined based on the first PPG signal, and the first heart rate with a high confidence is output according to the confidence output strategy, in other words, the first heart rate is output only when the confidence of the first heart rate meets the preset confidence condition, for example, the first heart rate is output only when the confidence of the first heart rate is higher than the confidence threshold. In this way, the high reliability of the output heart rate value can be ensured.

In this embodiment of this application, the confidence of the first heart rate is determined according to weight coefficients of M harmonic signals, where the M harmonic signals are determined according to the first PPG signal within a preset time, and M is an integer greater than or equal to 2. Duration or a measurement unit (or granularity) of the preset time is not specifically limited in this embodiment of this application.

Optionally, as a possible implementation, the M harmonic signals may be obtained according to the acquired first PPG signal, a weight coefficient of each harmonic signal may be calculated, and a confidence of the weight coefficient of each harmonic signal is determined, to obtain M confidences. And, a highest confidence among the M confidences is used as the confidence of the first heart rate.

That is, after the M confidences are obtained based on the M harmonic signals, the highest confidence is selected as the confidence of the first heart rate, so as to accurately reflect the heart rate of the user.

A specific manner of how to obtain the M harmonic signals according to the first PPG signal is not limited in this embodiment of this application. The M harmonic signals can be obtained by performing some transform processing on the first PPG signal and then performing harmonic decomposition on the transformed signal.

Optionally, in some possible embodiments, the following processing may be performed on the first PPG signal: smoothing processing, band-pass filtering processing, Hilbert transform, notching and de-noising, harmonic decomposition, and the like, to obtain a processed signal. Then, the processed signal is filtered through M filters to obtain the M harmonic signals.

In summary, the following processing is performed on the acquired first PPG signal: smoothing processing, band-pass filtering processing, Hilbert transform, notching and de-noising, and harmonic decomposition. The weight coefficient of each harmonic signal after the harmonic decomposition is calculated, and the confidence of the heart rate can be obtained by calculating the confidence based on the weight coefficient.

For ease of understanding, a process of determining the first heart rate and the confidence of the first heart rate according to the first PPG signal is described in detail below with reference to FIG. 3. FIG. 3 is a schematic flowchart of a confidence calculation method according to an embodiment of this application. As shown in FIG. 3, the method includes the following steps:

Step 301. Perform smoothing processing on the first PPG signal to obtain a PPG signal after the smoothing processing.

In a possible implementation, the first PPG signal is acquired by a PPG sensor at a frequency of 100 hz, that is, 100 frames of data are acquired per second and each frame of data takes 10 ms.

The smoothing processing may alternatively be understood as performing de-burring processing on the PPG signal. Expression forms of burrs include a dip and a spike.

It may be understood that both the dip and the spike are abnormal signals. A reason that the abnormal signals are generated is that: the user wears the watch excessively loosely, so that the acquired PPG signal is inaccurate. The dip refers to an excessively small signal; and the spike refers to an excessively large signal. As for how to identify the dip and the spike, in this embodiment of this application, a threshold can be set to identify the abnormal signals.

Optionally, as a possible implementation, a peak of the PPG signal can be identified by setting a ratio threshold. A value of the ratio threshold may be preset, and this application does not limit a specific value of the ratio threshold.

For example, in a case that a signal abnormality of a current frame is identified, a difference between data of the current frame and data of a previous frame is calculated, the difference is divided by the data of the previous frame to obtain a ratio, and the ratio is compared with the ratio threshold to obtain a comparison result. If the ratio is greater than or equal to the ratio threshold, it is determined that the data of the current frame is a peak, then smoothing processing needs to be performed on the data of the current frame. If the ratio is less than the ratio threshold, there is no need to perform smoothing processing on the data of the current frame.

In this embodiment of this application, a specific manner of performing smoothing processing on the peak of the PPG signal is not limited.

Optionally, as a possible implementation, if the data of the current frame is a peak, the performing smoothing processing on the data of the current frame includes: calculating a sum of data of a previous frame of the current frame and data of a next frame of the current frame, calculating an average value based on the sum, and using the average value as a value of the current frame after the smoothing processing.

For example, if a value of the current frame is 150, a value of the previous frame is 100, and a value of the next frame is 100, the value of the current frame after the smoothing processing is (100+100)/2=100.

Based on the foregoing manner, the situation of dip and spike is eliminated in the first PPG signal after the smoothing processing.

Step 302. Perform band-pass filtering on the PPG signal after the smoothing processing to obtain a second PPG signal, where the second PPG signal is a PPG signal in a target frequency band range.

The target frequency band range is determined according to a target heart rate range. The target heart rate range refers to a normal heart rate range.

For example, it can be learned from prior knowledge that the normal heart rate range is generally 30 beats/min to 240 beats/min, and accordingly, the target frequency band range can be set to 0.5 hz to 4 hz.

For example, herein, a band-pass filter is set to allow only a PPG signal with a frequency band of 0.5 hz to 4 hz to pass. That is, band-pass filtering is performed on the PPG signal after the smoothing processing at 0.5 hz to 4 hz to obtain a PPG signal with a frequency band of 0.5 hz to 4 hz (for example, referred to as the second PPG signal).

Step 303. Perform Hilbert transform on the second PPG signal to obtain an analytic signal of the second PPG signal. A derivative of a phase of the analytic signal is an instantaneous frequency.

The Hilbert transform refers to: transforming a real signal into an analytic signal. A result of transforming the real signal into the analytic signal is that a one-dimensional signal is transformed into a signal on a two-dimensional complex plane, and a magnitude and an argument of a complex number represent an amplitude and a phase of the signal. Herein, the instantaneous frequency can be obtained by deriving the phase of the analytic signal.

Optionally, as a possible implementation, a manner of calculating the first heart rate includes: deriving the phase of the analytic signal to obtain the heart rate value. Certainly, whether to output the heart rate value also needs to be determined with reference to the confidence of the heart rate.

Step 304. Perform notch processing on the analytic signal to obtain a third PPG signal. The notch processing is used to eliminate interference from motion noise. The third PPG signal is a signal obtained after notch processing. The third PPG signal does not include a motion interference signal.

A purpose of the notch processing is to eliminate the interference from the motion noise. The notch processing can be implemented through a notch filter. The notch filter refers to a filter that can rapidly attenuate an input signal at a certain frequency point to achieve a filtering effect of preventing the frequency signal from passing.

In general, the PPG signal acquired by the heart rate sensor further includes interference from an ACC signal. Using an application scenario as an example for description, this is because when the user wears the watch, in addition to pulse motion, an arm of the user may also move, so that the PPG signal acquired by the heart rate sensor also includes a signal generated by arm motion. The signal generated by the arm motion of the user is generally acquired by an acceleration sensor ACC. To eliminate an impact of the arm motion on the PPG signal, notch processing needs to be performed on the PPG signal in combination with an ACC dominant frequency to eliminate the interference from the ACC signal.

Step 305. Filter the third PPG signal through M filters to obtain M harmonic signals.

The M filters are narrow-band filters. After filtered by the M filters, the third PPG signal can be decomposed into the M harmonic signals.

For example, the third PPG signal obtains a harmonic signal 1 through a filter 1; the third PPG signal obtains a harmonic signal 2 through a filter 2; . . . ; and the third PPG signal obtains a harmonic signal M through a filter M.

After the M harmonic signals are obtained, a weight coefficient of each harmonic signal can be respectively calculated, and a confidence of the weight coefficient of each harmonic signal can be determined.

Step 306. Determine the weight coefficient of each of the M harmonic signals.

During a specific implementation, a weight coefficient of a relative error may be calculated by each harmonic signal in combination with an ideal signal.

Optionally, as a possible implementation, the determining the weight coefficient of each of the M harmonic signals includes:

calculating the relative error of each harmonic signal relative to the ideal signal;

dividing the relative error of each harmonic signal by a sum of relative errors of the M harmonic signals to obtain the weight coefficient of each harmonic signal.

It should be noted that, each of the harmonic signals has a corresponding ideal signal. The ideal signal can be defined as follows: the ideal signal can be obtained by multiplying a signal at a previous moment of a current moment by a phase at a next moment.

For example, the ideal signal can be represented as the following formula:

$$y^*[n] = e^{j\omega[n+1]} y[n-1]$$

$y^*[n]$ represents the ideal signal at an n moment, $y[n-1]$ represents a filtered signal at an $n-1$ moment, and $e^{j\omega[n+1]}$ represents a polar coordinate of a phase at a next moment.

For example, taking a harmonic signal 1 as an example, a relative error of the harmonic signal 1 and an ideal signal corresponding to the harmonic signal 1 is calculated to be $\Delta_1$, and a sum of the relative errors of the M harmonic signals is $\Delta_1 + \Delta_2 + \ldots \Delta_M$, so a weight coefficient of the harmonic signal 1 is $$\frac{\Delta_1}{\Delta_1 + \Delta_2 + \ldots \Delta_M}.$$

Step 307. Determine the confidence of the weight coefficient of each harmonic signal.

A confidence interval threshold is determined according to big data sample statistics, thereby dividing a confidence level. That is, the confidence interval threshold may be determined by big data sample statistics. After the weight coefficient of each harmonic signal is obtained, the confidence corresponding to the weight coefficient can be determined according to the confidence interval threshold.

Optionally, a certain amount of sample data can be acquired and four levels of confidence interval thresholds can be obtained by division according to a quartile method, to convert the weight coefficient to the confidence. When the value of the confidence is higher, it indicates that the data is more reliable; and when the value of the confidence is lower, it indicates that the data is more unreliable. For example, it is assumed that the confidence is divided into four levels from low to high: 0, 1, 2, and 3, confidences whose values are greater than or equal to 2 are determined as a high confidence interval, and confidences whose values are less than 2 are determined as a low confidence interval.

Quartile refers to a value at three division points after all pieces of sample data are sorted according to the magnitudes and are divided into four equal parts. There are three quartiles. A first quartile is a commonly known quartile, and is referred to as a lower quartile, a second quartile is a median, and a third quartile is referred to as an upper quartile. The first quartile, the second quartile, and the third quartile are represented as Q1, Q2, and Q3 respectively.

Descriptions are made below with reference to examples in Table 1. It is assumed that 10,000 groups of sample data are acquired, and the 10,000 groups of data are divided according to the quartile method. Values of three quartiles of the quartile are 1000, 100, and 10 respectively. A correspondence between the weight coefficient and the confidence interval is shown in Table 1 below:

TABLE 1

| Weight coefficient | Confidence interval |
| --- | --- |
| Greater than 1000 | 0 |
| Greater than 100 and less than or equal to 1000 | 1 |
| Greater than 10 and less than or equal to 100 | 2 |
| Less than or equal to 10 | 3 |

In Table 1, the confidence is divided into four levels, and the confidence levels sequentially increase from 0 to 3. Taking the data in the third row in Table 1 as an example, if a value of the weight coefficient is a number greater than 10 and less than or equal to 100, a corresponding confidence of 2 can be obtained through Table 1.

It should be understood that during specific implementation, a corresponding confidence interval may be formulated according to sample data of different scenarios (such as sleep, running, walking, yoga, and the like), or a unified confidence interval standard may be formulated. This is not specifically limited in this embodiment of this application.

It should also be understood that the example in Table 1 is merely an example for description, and does not constitute a limitation on this embodiment of this application.

As described above, the confidence of the weight coefficient of each harmonic signal can be obtained through the process shown in FIG. 3, thereby obtaining the M confidences. Further, a highest confidence value among the M confidences can be used as the confidence of the heart rate.

A software system and hardware architecture to which the embodiments of this application are applied are respectively described below with reference to FIG. 4 and FIG. 5.

Figure 4:
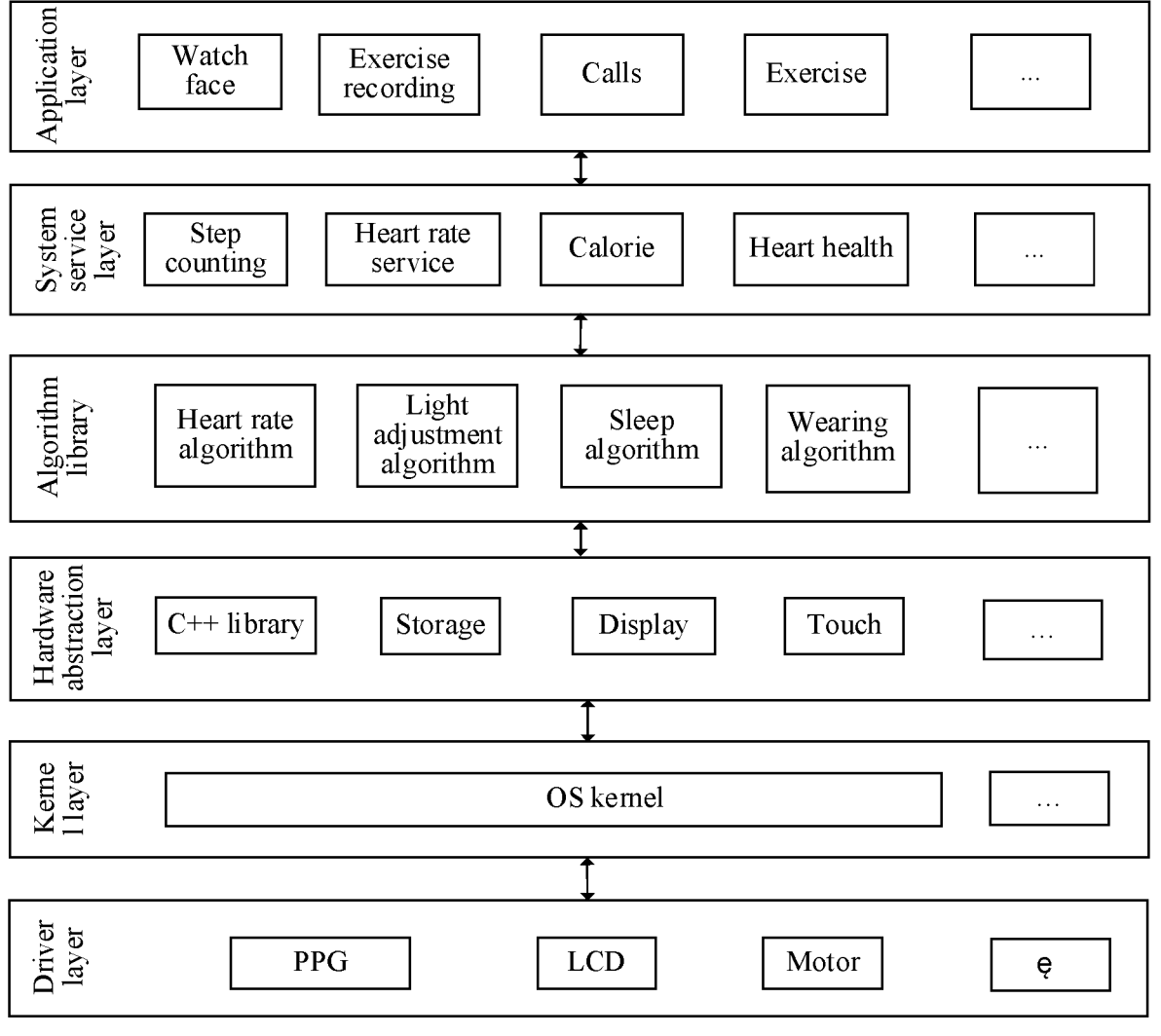
FIG. 4 is a schematic diagram of a software system to which an embodiment of this application is applied.

FIG. 4 is a schematic diagram of a software system to which an embodiment of this application is applied. As shown in FIG. 4, the software system using a layered architecture is divided into several layers, and each layer has a clear role and task. The layers communicate with each other through a software interface. In some embodiments, the software system may be divided into six layers, namely an application layer, a system service layer, an algorithm library (library), a hardware abstraction layer HAL, a kernel layer (kernel), and a driver layer (driver).

As shown in FIG. 4, the application layer includes a watch face, exercise recording, calls, and exercise.

It may be understood that, partial applications are shown in FIG. 4, and in fact the application layer may further include other applications, which is not limited in this application. For example, the application layer further includes applications such as message, alarm clock, weather, stopwatch, compass, timer, flashlight, calendar, and Alipay.

As shown in FIG. 4, the system service layer includes step counting, heart rate service, calorie, heart health, and the like.

The algorithm library may include a plurality of algorithmic modules. For example, as shown in FIG. 4, the algorithm library includes a heart rate algorithm module, a light adjustment algorithm module, a sleep algorithm, a wearing algorithm, and the like.

The heart rate algorithm module is configured to determine a first heart rate and a confidence of the first heart rate. As a possible implementation, the heart rate algorithm module is configured to perform step 204, or configured to perform the foregoing method shown in FIG. 3.

The wearing algorithm is used to detect a wearing state of the watch. As a possible implementation, the wearing algorithm module is configured to perform step 203.

As shown in FIG. 4, the hardware abstraction layer includes a C++ library, storage, display, touch, and the like. The C++ library is used to provide system resources for the algorithm library.

It may be understood that the hardware abstraction layer shown in FIG. 4 is partial content, and in fact the hardware abstraction layer HAL may further include other content, such as a Bluetooth module, a GPS module, and the like.

As shown in FIG. 4, the kernel layer includes an OS kernel. The OS kernel is used to perform management and scheduling.

The driver layer is used to drive hardware resources. The driver layer may include a plurality of driver modules. As shown in FIG. 4, the driver layer includes a PPG driver, an LCD driver, a motor, and the like.

For example, a user can click on an exercise application. As the user is exercising, the exercise application can display the heart rate to the user in real time through an interface. A process of generating a heart rate according to this embodiment of this application is described below with reference to FIG. 4. When the user clicks on the exercise application, the application program layer calls the heart rate service in the system service layer after receiving an operation of the user. The OS kernel schedules the PPG driver, so that the PPG sensor lights up to acquire data (or a PPG signal). The PPG driver can return the acquired data to the OS kernel. The OS kernel sends the acquired data to the algorithm library to perform a relevant calculation. The wearing algorithm module in the algorithm library detects whether the watch is worn based on the PPG signal and reports a wearing result to the OS kernel. If it is detected that the user wears the watch, the OS kernel triggers the execution of a heart rate monitoring service. The OS kernel sends the data, acquired by making the PPG sensor light up, to the heart rate algorithm module. The heart rate algorithm module calculates the heart rate and the confidence of the heart rate based on the PPG signal. The heart rate algorithm module returns the heart rate value and the confidence of the heart rate to the OS kernel. The OS kernel determines heart rate values with a high confidence according to a confidence output strategy. The OS kernel reports the heart rate values with a high confidence to the application layer. The application layer displays the heart rate values reported by the OS kernel on the UI interface.

Optionally, the OS kernel stores the heart rate values with a high confidence. The application layer generates a heart rate curve according to the plurality of heart rate values with a high confidence reported by the OS kernel, and displays the heart rate curve on the UI interface.

Optionally, the application layer may further receive an end trigger operation of the user, where the end trigger operation is used to end heart rate monitoring. After obtaining the end trigger operation of the application layer, the OS kernel can schedule the heart rate algorithm module and wearing algorithm module in the algorithm library to end the operation. After the heart rate algorithm module and wearing algorithm module end the operation, the ending may be reported to the OS kernel. The OS kernel schedules the PPG driver to make the PPG sensor perform a light-off operation.

Figure 5:
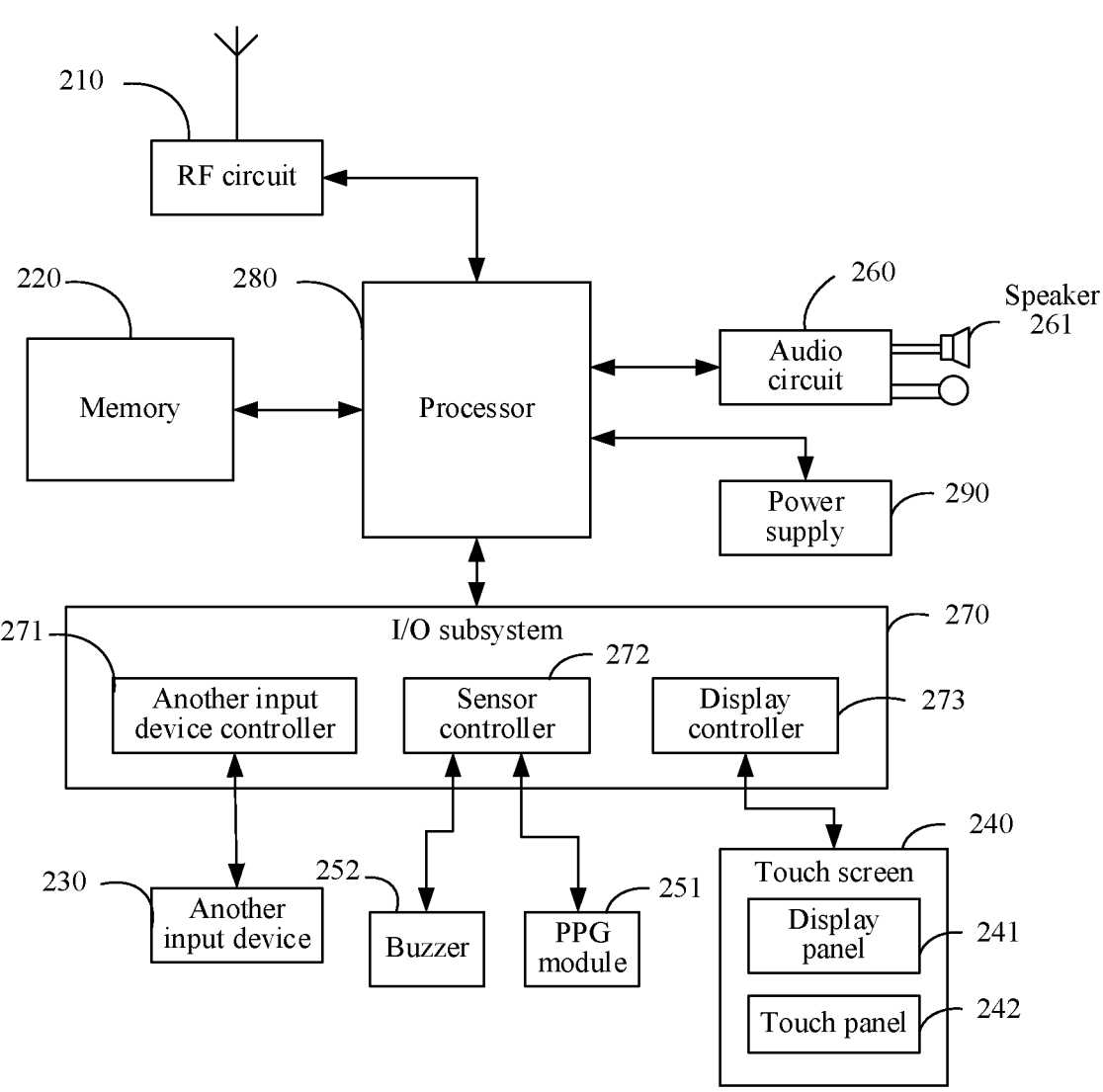
FIG. 5 is a schematic diagram of a structure to which an embodiment of this application is applied.

FIG. 5 is a schematic structural diagram of an apparatus 500 applied to an embodiment of this application. The apparatus 500 may be a watch, a wristband, a wearable electronic device, another wearable device for measuring a heart rate, or the like. The specific type of the apparatus 500 is not limited in this embodiment of this application.

As shown in FIG. 5, the apparatus 500 may include components such as a radio frequency (radio frequency, RF) circuit 210, a memory 220, another input device 230, a touch screen 240, a PPG module 251, a buzzer 252, an audio circuit 260, an I/O subsystem 270, a processor 280, a power source 290, and the like.

It should be noted that, the structure shown in FIG. 5 does not constitute a specific limitation on the apparatus 500. In some other embodiments of this application, the apparatus 500 may include more or fewer components than the components shown in FIG. 5, or the apparatus 500 may include a combination of some components in the components shown in FIG. 5, or the apparatus 500 may include sub-components of some components in the components shown in FIG. 5. The components shown in FIG. 5 may be implemented by hardware, software, or a combination of software and hardware.

The RF circuit 210 may be configured to send and receive signals during an information receiving and sending process or a call process. For example, after downlink information of a base station is received, the downlink information is sent to the processor 280 for processing. In addition, uplink data is sent to the base station. Generally, the RF circuit includes, but is not limited to, an antenna, at least one amplifier, a transceiver, a coupler, a low noise amplifier (low noise amplifier, LNA), a duplexer, and the like. In addition, the RF circuit 210 may also communicate with a network and another device through wireless communication. The wireless communication may use any communication standard or protocol, which includes, but is not limited to, Global System for Mobile Communications (global system of mobile communication, GSM), General Packet Radio Service (general packet radio service, GPRS), Code Division Multiple Access (code division multiple access, CDMA), Wideband Code Division Multiple Access (wideband code division multiple access, WCDMA), Long Term Evolution (long term evolution, LTE), e-mail, a short messaging service (short messaging service, SMS), and the like.

The memory 220 may be configured to store a software program. By running the software program stored in the memory 220, the processor 280 performs various functions of the apparatus 500. The memory 220 may mainly include a program storage area and a data storage area. The program storage area may store an operating system, an application program required by at least one function (such as a sound playback function and an image display function), and the like. The data storage area may store data (such as audio data and an address book) maintained according to use of the apparatus 500, and the like. In addition, the memory 220 may include a high speed random access memory, and may further include a non-volatile memory, such as at least one magnetic disk storage device, a flash storage device, or another volatile solid-state storage device.

The another input device 230 may be configured to receive input digit or character information, and generate a keyboard signal input related to user setting and function control of the apparatus 500. Specifically, the another input device 230 may include but is not limited to one or more of a physical keyboard, a function key (for example, a volume control key or a power on/off key), a trackball, a mouse, a joystick, and an optical mouse (the optical mouse is a touch-sensitive surface that does not display a visible output, or an extension of a touch-sensitive surface formed by a touch screen). The another input device 230 is connected to another input device controller 271 of the I/O subsystem 270, and exchanges a signal with the processor 280 under control of the another device input controller 271.

The touch screen 240 may be configured to display information entered by a user or information provided to the user, and various menus of the apparatus 500, and may further receive a user input. Specifically, the touch screen 240 may include a display panel 241 and a touch panel 242. The display panel 241 may be a liquid crystal display (liquid crystal display, LCD), an organic light-emitting diode (organic light-emitting diode, OLED), an active-matrix organic light-emitting diode (active-matrix organic light-emitting diode, AMOLED), a flex light-emitting diode (flex light-emitting diode, FLED), a mini light-emitting diode (mini light-emitting diode, Mini LED), a micro light-emitting diode (micro light-emitting diode, Micro LED), a micro OLED (Micro OLED), or a quantum dot light emitting diode (quantum dot light emitting diodes, QLED).

The touch panel 242 is also referred to as a display screen, a touch-sensitive screen, or the like, and may collect a contact or non-contact operation of a user on or near the touch panel 242 (such as an operation of the user on or near the touch panel 242 by using any suitable object or attachment, such as a finger or a touch pen, or including a motion sensing operation, where the operation includes a single-point control operation, a multi-point control operation, or another type of operation), and drive a corresponding connecting apparatus according to a preset program. Optionally, the touch panel 242 may include two parts: a touch detection apparatus and a touch controller. The touch detection apparatus detects a gesture of the user, that is, a touch position and posture, detects a signal generated by the touch operation, and transmits the signal to the touch controller. The touch controller receives touch information from the touch detection apparatus, converts the touch information into information that can be processed by the processor, and then transmits the information to the processor 280, and can receive and execute a command transmitted by the processor 280. In addition, the touch panel 242 may be implemented in various types, such as a resistive type, a capacitive type, an infrared type, or a surface sound wave type, or the touch panel 242 may be implemented by using any technology developed in the future. Further, the touch panel 242 may cover the display panel 241. The user may perform, according to content displayed (the displayed content includes, but is not limited to, a soft keyboard, a virtual mouse, a virtual key, an icon, and the like) on the display panel 241, an operation on or near the touch panel 242 covering the display panel 241. After detecting the operation on or near the touch panel 242, the touch panel 242 transmits the operation to the processor 280 through the I/O subsystem 270, to determine the user input. Subsequently, the processor 280 provides a corresponding visual output on the display panel 241 through the I/O subsystem 270 according to the user input. Although, in FIG. 5, the touch panel 242 and the display panel 241 are used as two separate components to implement input and output functions of the apparatus 500, in some embodiments, the touch panel 242 and the display panel 241 may be integrated to implement the input and output functions of the apparatus 500.

Prompt information such as a wearing manner and wearing state, and historical information of a visual form (number, table, and graphic) or an audible form (synthetic speech or tune) of detected heart rate may be provided on the display panel 241 under control of a program of the processor 280. As a non-limiting example, a visual graph may be displayed. The visual graph shows the heart rate calculated every 5 minutes at a previous fixed time interval (for example, 1 hour) or after an exercise period has ended (for example, determined by an instruction from the user). Average heart rate information or heart rate statistical information during a previous time period or a plurality of time periods may further be provided on the display panel 241 under control of the processor 280. As another example, a current heart rate value may be provided on the display panel 241 as a "real-time" heart rate value that is periodically (for example, per second) displayed to the user during an ongoing exercise plan.

The PPG module 251 includes a light emitter and a light sensor. The measurement of heart rate by the PPG module is based on the principle of light absorption by substances. The light emitter in the PPG module of the electronic device irradiates blood vessels of skin, and the light sensor receives light transmitted from the skin. Since different volumes of blood in the blood vessels absorb green light differently, at the time of heart beating, the blood flow increases, and the amount of absorbed green light increases accordingly; and at the time of interval between two heart beats, the blood flow decreases, and the amount of absorbed green light decreases accordingly. Therefore, the heart rate can be measured according to light absorbance of the blood. In operation, the light emitter may transmit a light beam to the skin of the user, and the light beam may be reflected by the skin of the user and received by the light sensor. The light sensor may convert the light into an electrical signal that indicates intensity of the light. The electrical signal may be in an analog form and may be converted to a digital form by an analog-to-digital converter. A digital signal from the analog-to-digital converter may be a time-domain PPG signal fed to the processor 280. An output of an accelerometer may further be converted to a digital form by the analog-to-digital converter. The processor 280 may receive a digital signal from the light sensor, and digitize an accelerometer output signal of the accelerometer, and may process the signals to provide a heart rate or wearing state output signal to a storage device, a visual display, an audible annunciator, the touch screen, or another output indicator.

The apparatus 500 may further include at least one sensor such as the light sensor, a motion sensor, and other sensors. Specifically, the light sensor may include an ambient light sensor and a proximity sensor, where the ambient light sensor may adjust luminance of the display panel 241 according to brightness of ambient light. The proximity sensor may switch off backlight of the display panel 241 and/or the touch panel 242 when the apparatus 500 is moved to an ear. As a type of motion sensor, an accelerometer sensor may detect a magnitude of acceleration in various directions (generally three axes), and may detect a magnitude and a direction of gravity when static, which may be used for a function related to vibration identification (such as a pedometer and a knock), and the like. For other sensors such as a gyroscope, a barometer, a hygrometer, a thermometer, an infrared sensor, and the like that may further be configured on the apparatus 500, details are not described herein again.

The apparatus 500 may further include the buzzer 252, which may generate vibrations according to an instruction of the processor 280.

The audio circuit 260 may provide an audio interface between the user and the apparatus 500. The audio circuit 260 may transmit the received converted audio data into a speaker 261. The speaker 261 converts the signal into a sound signal and output the sound signal. On the other hand, a microphone converts the collected sound signal into a signal. The audio circuit 260 receives the signal, converts the signal into the audio data, and then outputs the audio data to the RF circuit 210 to send the audio data to, for example, a mobile phone, or outputs the audio data to the memory 220 for further processing.

The I/O subsystem 270 is configured to control external input and output devices, and may include the another device input controller 271, a sensor controller 272, and a display controller 273. Optionally, one or more another input control device controllers 271 receive a signal from the another input device 230 and/or send a signal to the another input device 230. The another input device 230 may include a physical button (a pressing button, a rocker button, and the like), a dial pad, a slider switch, a joystick, a click scroll wheel, or an optical mouse (the optical mouse may be a touch-sensitive surface that does not display a visible output, or an extension of a touch-sensitive surface formed by a touch screen). It should be noted that the another input control device controller 271 may be connected to any one or more of the foregoing devices. The display controller 273 in the I/O subsystem 270 receives a signal from the touch screen 240 or sends a signal to the touch screen 240. After the touch screen 240 detects the user input, the display controller 273 converts the detected user input into interaction with an object displayed on a user interface of the touch screen 240. That is, man-machine interaction is implemented. The sensor controller 272 may receive a signal from one or more sensors 251 and/or may send a signal to the one or more sensors 251.

The processor 280 is a control center of the apparatus 500, and is connected to various parts of the mobile phone by using various interfaces and lines. By running or executing the software program and/or modules stored in the memory 220, and invoking data stored in the memory 220, the processor 280 performs various functions and data processing of the apparatus 500. Optionally, the processor 280 may include one or more processing units. For example, the processor 110 may include at least one of the following processing units: an application processor (application processor, AP), a modem processor, a graphics processing unit (graphics processing unit, GPU), an image signal processor (image signal processor, ISP), a controller, a video codec, a digital signal processor (digital signal processor, DSP), a baseband processor, and a neural-network processing unit (neural-network processing unit, NPU). Different processing units may be independent components, or may be integrated components.

Optionally, the processor 280 may integrate the application processor and the modem processor. The application processor mainly processes an operating system, a user interface, an application, and the like. The modem processor mainly processes wireless communication. It may be understood that the modem processor may alternatively not be integrated into the processor 280.

The apparatus 500 further includes the power supply 290 (such as a battery) for supplying power to the components. Optionally, the power supply may be logically connected to the processor 280 through a power management system, thereby implementing functions such as charging, discharging, and power consumption management through the power management system. It should be understood that, although not shown in the figure, the apparatus 500 may further include a camera, a Bluetooth module, and the like, and details are not described herein.

The modules stored in the memory 220 may include: an operating system, a contact/motion module, a graphic module, applications, and the like.

The contact/motion module is configured to detect contact of an object or a finger with the touch screen 240 or a click-type touch wheel, capture a speed (direction and magnitude) and an acceleration (a change in magnitude or direction) of the contact, and determine the type of a contact event. For example, there are a plurality of contact event detection modules, and sometimes a gesture is combined with an element in the user interface to implement some operations: finger pinching/depinching (pinching/depinching), and the like.

The graphic module is configured to render and display a graphic on the touch screen or another display, where the graphic includes a web page, an icon, a digital image, a video, and an animation.

The applications may include contacts, phone, video conference, email client, instant messaging, personal motion, camera, image management, video player, music player, calendar, plug-ins (for example, weather, stocks, calculator, clock, and dictionary), custom plug-ins, search, note, map, online video, and the like.

It may be understood that, a connection relationship between the modules shown in FIG. 5 is merely an example for description, and does not constitute a limitation on the connection relationship between the modules of the apparatus 500. Optionally, the modules of the apparatus 500 may alternatively be a combination in the plurality of connection manners in the foregoing embodiments.

For ease of understanding, the following is described with reference to interfaces in FIG. 6 and FIG. 7. It should be understood that the interfaces shown in FIG. 6 and FIG. 7 do not constitute a limitation on the embodiments of this application.

Figure 6:
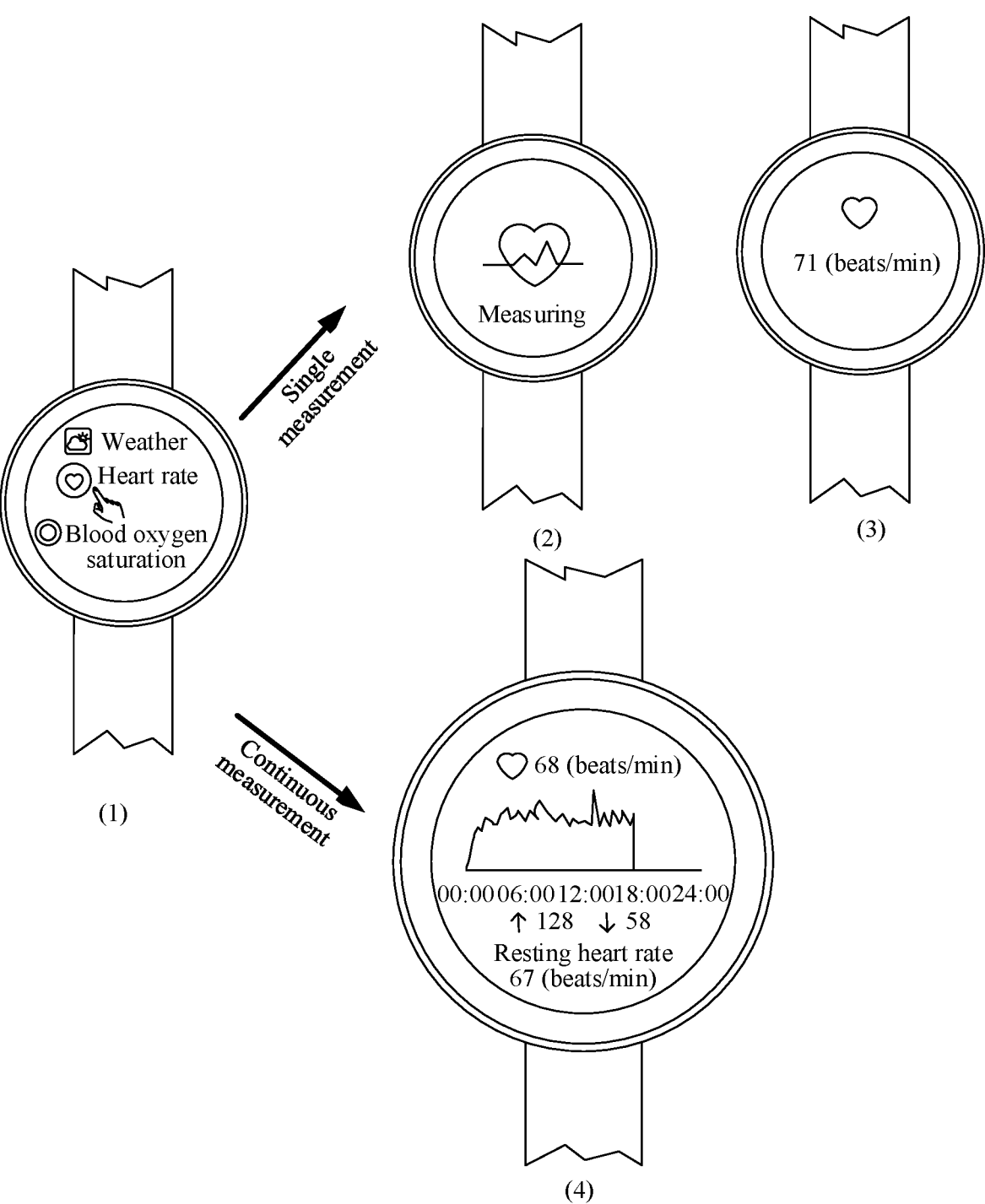
FIG. 6 is an exemplary diagram of an interface of heart rate monitoring according to an embodiment of this application.

FIG. 6 is an exemplary diagram of an interface of heart rate monitoring according to an embodiment of this application.

As shown in (1) in FIG. 6, in a state that the user wears the watch, the user can click on a heart rate application in an interface of the watch. The heart rate application can perform a single heart rate measurement. It should be understood that the interface of (1) in FIG. 6 shows only icons of part of applications, such as weather and blood oxygen saturation, but this does not constitute a limitation on this embodiment of this application.

In a case of single heart rate measurement, the interface of the watch is shown in (2) in FIG. 6, showing that the watch is measuring the heart rate. As shown in (3) in FIG. 6, the watch can present the user with a heart rate value that is detected in real time, for example, 71 beats/min.

In this embodiment of this application, even though the user wears the watch relatively loosely, the watch can still present the user with a relatively accurate heart rate value.

As a possible embodiment, a heart rate value with a high confidence shown in (3) in FIG. 6 is output by calculating a confidence of the heart rate.

In a possible implementation, the user can enable an option of continuous heart rate measurement through a mobile phone. After the option of continuous heart rate measurement is enabled, the watch performs user heart rate monitoring for 24 hours, and can display a 24-hour heart rate curve and resting heart rate.

In a case of continuous heart rate measurement, the interface of the watch may be shown in (4) in FIG. 6. In the interface shown in (4) in FIG. 6, the watch may present the user with a heart rate curve and resting heart rate within a certain time period.

As a possible embodiment, the heart rate curve shown in (4) in FIG. 6 may be generated by a plurality of heart rate values with a high confidence.

Figure 7:
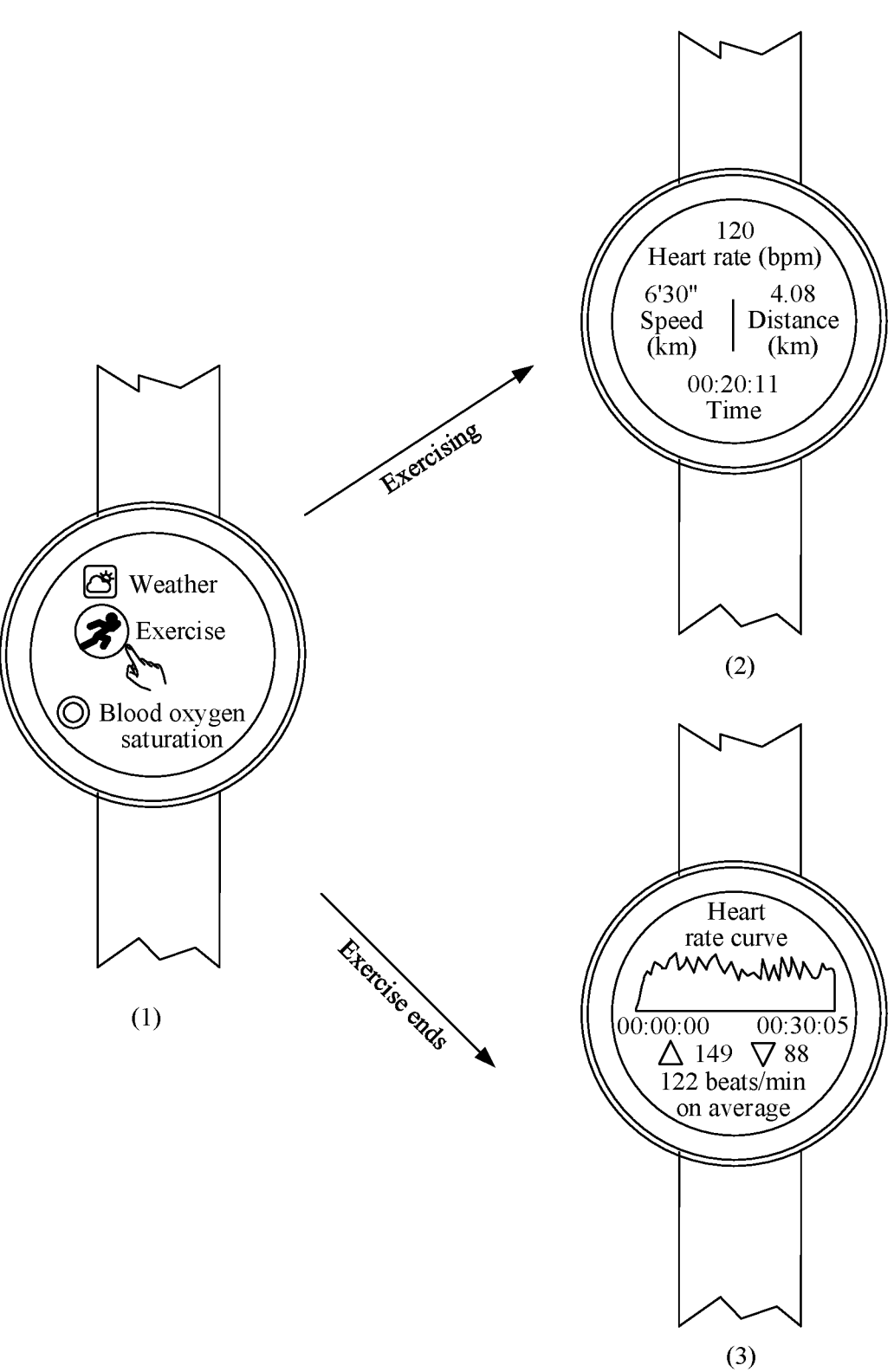
FIG. 7 is an exemplary diagram of another interface of heart rate monitoring according to an embodiment of this application.

FIG. 7 is an exemplary diagram of another interface of heart rate monitoring according to an embodiment of this application.

As shown in (1) in FIG. 7, in a state that the user wears the watch, the user can click on an exercise application in an interface of the watch to start the exercise application to monitor information during exercise. During the exercise, the watch can display exercise information in the exercise application in real time. For example, as shown in an interface shown in (2) in FIG. 7, the watch can present a heart rate value, speed, distance, time, and the like to the user.

As a possible embodiment, a heart rate value with a high confidence shown in (2) in FIG. 7 can be output by calculating a confidence of a heart rate.

After the exercise ends, the user can view a heart rate curve during the exercise. As an interface shown in (3) in FIG. 7, the watch can present the user with information such as the heart rate curve, an average heart rate, a highest heart rate, and a lowest heart rate.

As a possible embodiment, the heart rate curve shown in (3) in FIG. 7 can be generated by a plurality of heart rate values with a high confidence.

Effects of performing signal optimization according to the embodiments of this application are described below with reference to FIG. 8 and FIG. 9.

Figure 8:
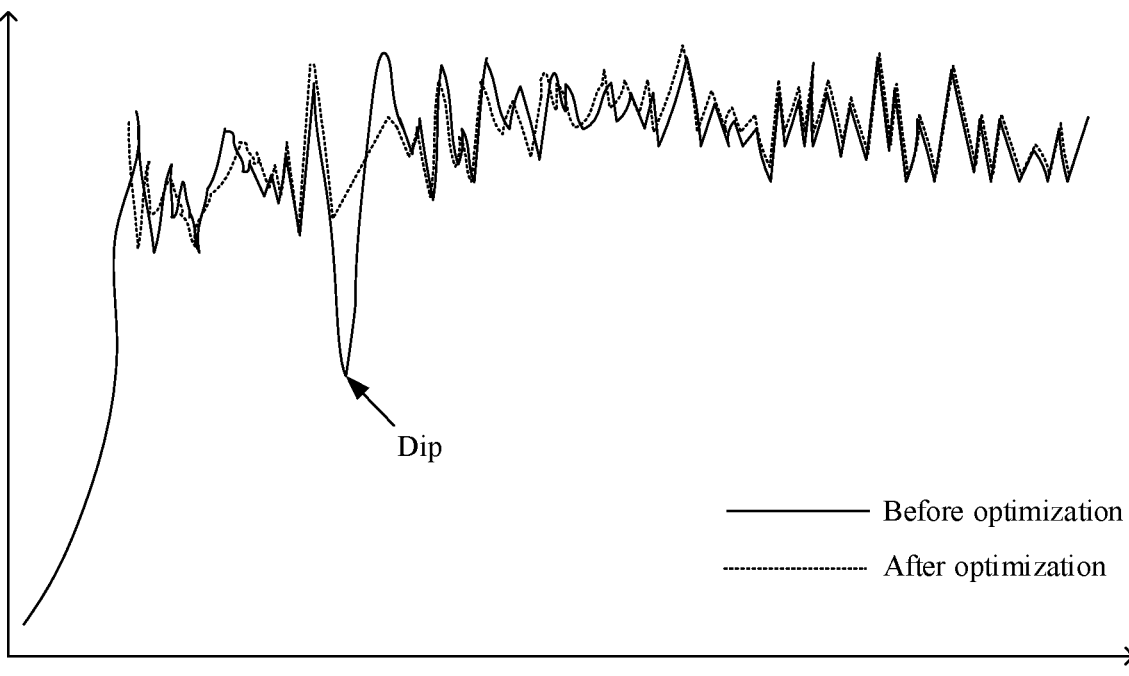
FIG. 8 is a schematic diagram of effect comparison of optimizing a dip signal according to an embodiment of this application.

FIG. 8 is a schematic diagram of effect comparison of optimizing a dip signal according to an embodiment of this application. As shown in FIG. 8, the solid line represents a PPG signal before optimization; and the dashed line represents an optimized PPG signal. It can be seen that a dip signal exists obviously in the PPG signal before optimization, and after algorithm optimization of this embodiment of this application, the dip signal is removed from the PPG signal.

Figure 9:
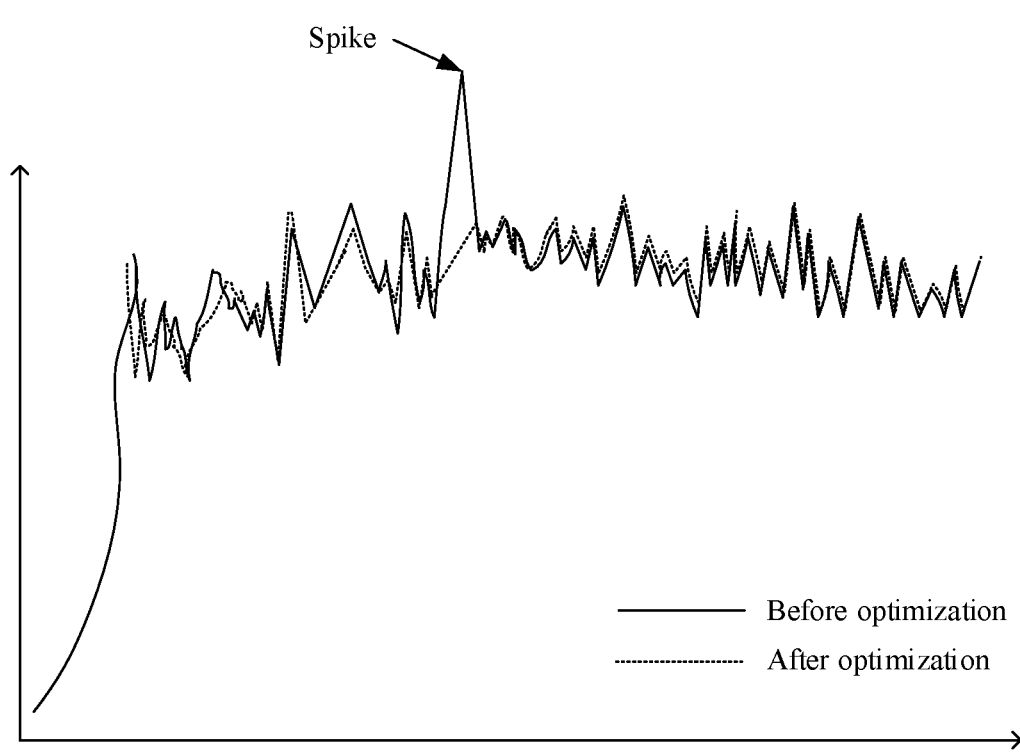
FIG. 9 is a schematic diagram of effect comparison of optimizing a spike signal according to an embodiment of this application.

FIG. 9 is a schematic diagram of effect comparison of optimizing a spike signal according to an embodiment of this application. As shown in FIG. 9, the solid line represents a PPG signal before optimization; and the dashed line represents an optimized PPG signal. It can be seen that a spike signal exists obviously in the PPG signal before optimization, and after algorithm optimization of this embodiment of this application, the spike signal is removed from the PPG signal.

It should be understood that the examples in FIG. 8 and FIG. 9 are result comparison diagrams of algorithm simulation of the embodiments of this application, and do not constitute a limitation on the embodiments of this application.

This application further provides a computer program product, where the computer program product, when executed by a processor, implements the method according to any method embodiment of this application.

The computer program product may be stored in a memory, and subjected to processing procedures such as preprocessing, compiling, assembling, and linking, to be eventually converted into an executable target file that can be executed by the processor.

This application further provides a computer-readable storage medium, storing a computer program, where the computer program, when executed by a computer, implements the method according to any method embodiment of this application. The computer program may be a high-level language program or an executable target program.

The computer-readable storage medium may be a volatile memory or non-volatile memory, or may include both a volatile memory and a non-volatile memory. The non-volatile memory may be a read-only memory (read-only memory, ROM), a programmable ROM (programmable ROM, PROM), an erasable PROM (erasable PROM, EPROM), an electrically EPROM (electrically EPROM, EEPROM), or a flash memory. The volatile memory may be a random access memory (random access memory, RAM), and is used as an external cache. Through example but not limitative description, many forms of RAMs may be used, for example, a static RAM (static RAM, SRAM), a dynamic RAM (dynamic RAM, DRAM), a synchronous DRAM (synchronous DRAM, SDRAM), a double data rate SDRAM (double data rate SDRAM, DDR SDRAM), an enhanced SDRAM (enhanced SDRAM, ESDRAM), a synchlink DRAM (synchlink DRAM, SLDRAM), and a direct rambus RAM (direct rambus RAM, DR RAM).

It may be clearly understood by a person skilled in the art that, for ease and brief description, for a detailed working process and a generated technical effect of the foregoing apparatus and device, reference may be made to a corresponding process and technical effect in the foregoing method embodiment, and details are not described herein again In the several embodiments provided in this application, the disclosed system, apparatus, and method may be implemented in other manners. For example, some features of the method embodiment described above may be ignored or not be performed. The described apparatus embodiment is merely exemplary. The unit division is merely logical function division and may be other division during actual implementation, and a plurality of units or components may be combined or integrated into another system. In addition, the coupling between the units or the coupling between the components may be direct coupling or indirect coupling, and the coupling includes an electrical connection, a mechanical connection, or another form of connection.

It should be understood that sequence numbers of the processes do not mean execution sequences in various embodiments of this application. The execution sequences of the processes should be determined according to functions and internal logic of the processes, and should not constitute any limitation on the implementation processes of the embodiments of this application.

In addition, the terms "system" and "network" may be used interchangeably in this specification. The term "and/or" used in this specification describes only an association relationship for describing associated objects and represents that three relationships may exist. For example, A and/or B may represent the following three cases: only A exists, both A and B exist, and only B exists. In addition, the character "/" in this specification generally indicates an "or" relationship between the associated objects.

In summary, the foregoing descriptions are merely preferable embodiments of the technical solutions of this application, but are not intended to limit the protection scope of this application. Any modification, equivalent replacement, or improvement made without departing from the spirit and principle of this application shall fall within the protection scope of this application.

What is claimed is:

1. A method, applied to an electronic device, and comprising:

determining that a wearer of the electronic device is a living body;

obtaining a first photoplethysmograph (PPG) signal;

determining a first heart rate and a confidence of the first heart rate according to the first PPG signal, wherein the confidence of the first heart rate is determined based on weight coefficients of M harmonic signals, wherein the M harmonic signals are determined according to the first PPG signal within a preset time, and M is an integer greater than or equal to 2, the determining the first heart rate and the confidence of the first heart rate comprising:

performing smoothing processing on the first PPG signal to obtain a smoothed PPG signal after the smoothing processing, performing band-pass filtering on the smoothed PPG signal after the smoothing processing to obtain a second PPG signal, wherein the second PPG signal is in a target frequency band range, performing Hilbert transform on the second PPG signal to obtain an analytic signal of the second PPG signal, wherein a derivative of a phase of the analytic signal is an instantaneous frequency, performing notch processing on the analytic signal to obtain a third PPG signal, wherein the third PPG signal does not comprise a motion interference signal, and filtering the third PPG signal through M filters to obtain the M harmonic signals;

outputting the first heart rate based on the confidence of the first heart rate meeting a preset confidence condition; and displaying the first heart rate.

2. The method according to claim 1, further comprising:

displaying a second heart rate based on the confidence of the first heart rate not meeting the preset confidence condition, wherein the second heart rate is a heart rate that meets the preset confidence condition last time.

3. The method according to claim 1, further comprising:

calculating a corresponding weight coefficient of each of the M harmonic signals;

determining a corresponding confidence of the corresponding weight coefficient of each of the M harmonic signals to obtain M confidences; and using a highest confidence among the M confidences as the confidence of the first heart rate.

4. The method according to claim 3, wherein the calculating the corresponding weight coefficient of each of the M harmonic signals comprises:

calculating a relative error of each harmonic signal relative to an ideal signal, wherein the ideal signal is obtained by multiplying a previous signal at a previous moment of a current moment by a phase at a next moment; and dividing the relative error of each harmonic signal by a sum of relative errors of the M harmonic signals to obtain the corresponding weight coefficient of each of the M harmonic signals.

5. The method according to claim 3, wherein the determining the corresponding confidence of the corresponding weight coefficient of each of the M harmonic signals comprises:

determining the corresponding confidence corresponding to the corresponding weight coefficient of each of the M harmonic signals according to a confidence interval threshold, wherein the confidence interval threshold is determined by big data sample statistics.

6. The method according to claim 1, wherein the performing the smoothing processing on the first PPG signal to obtain a PPG signal after the smoothing processing comprises:

calculating, based on a signal abnormality of a current frame being identified, a sum of data of a previous frame of the current frame and data of a next frame of the current frame, and calculating an average value based on the sum of the data of the previous frame of the current frame and the data of the next frame of the current frame; and using the average value as a value of the current frame after the smoothing processing.

7. The method according to claim 1, wherein the confidence of the first heart rate meeting the preset confidence condition comprises:

the confidence of the first heart rate being greater than a confidence threshold.

8. The method according to claim 1, further comprising:

storing a plurality of heart rate values whose confidences meet the preset confidence condition;

generating a heart rate curve based on the plurality of heart rate values; and displaying the heart rate curve.

9. An electronic device, comprising:

a processor; and a memory coupled to the processor, the memory storing a computer program that, when executed by the processor, causes the electronic device to perform operations including:

determining that a wearer of the electronic device is a living body;

obtaining a first photoplethysmograph (PPG) signal;

determining a first heart rate and a confidence of the first heart rate according to the first PPG signal, wherein the confidence of the first heart rate is determined based on weight coefficients of M harmonic signals, wherein the M harmonic signals are determined according to the first PPG signal within a preset time, and M is an integer greater than or equal to 2, the determining the first heart rate and the confidence of the first heart rate comprising:

performing smoothing processing on the first PPG signal to obtain a smoothed PPG signal after the smoothing processing, performing band-pass filtering on the smoothed PPG signal after the smoothing processing to obtain a second PPG signal, wherein the second PPG signal is in a target frequency band range, performing Hilbert transform on the second PPG signal to obtain an analytic signal of the second PPG signal, wherein a derivative of a phase of the analytic signal is an instantaneous frequency, performing notch processing on the analytic signal to obtain a third PPG signal, wherein the third PPG signal does not comprise a motion interference signal, and filtering the third PPG signal through M filters to obtain the M harmonic signals;

outputting the first heart rate based on the confidence of the first heart rate meeting a preset confidence condition; and displaying the first heart rate.

10. The electronic device according to claim 9, the operations further comprising:

displaying a second heart rate based on the confidence of the first heart rate not meeting the preset confidence condition, wherein the second heart rate is a heart rate that meets the preset confidence condition last time.

11. The electronic device according to claim 9, the operations further comprising:

calculating a corresponding weight coefficient of each of the M harmonic signals;

determining a corresponding confidence of the corresponding weight coefficient of each of the M harmonic signals to obtain M confidences; and using a highest confidence among the M confidences as the confidence of the first heart rate.

12. The electronic device according to claim 11, wherein the calculating the corresponding weight coefficient of each of the M harmonic signals comprises:

calculating a relative error of each harmonic signal relative to an ideal signal, wherein the ideal signal is obtained by multiplying a previous signal at a previous moment of a current moment by a phase at a next moment; and dividing the relative error of each harmonic signal by a sum of relative errors of the M harmonic signals to obtain the corresponding weight coefficient of each of the M harmonic signals.

13. The electronic device according to claim 11, wherein the determining the corresponding confidence of the corresponding weight coefficient of each of the M harmonic signals comprises:

determining the corresponding confidence corresponding to the corresponding weight coefficient of each of the M harmonic signals according to a confidence interval threshold, wherein the confidence interval threshold is determined by big data sample statistics.

14. The electronic device according to claim 9, wherein the performing the smoothing processing on the first PPG signal to obtain a PPG signal after the smoothing processing comprises:

calculating, based on a signal abnormality of a current frame being identified, a sum of data of a previous frame of the current frame and data of a next frame of the current frame, and calculating an average value based on the sum of the data of the previous frame of the current frame and the data of the next frame of the current frame; and using the average value as a value of the current frame after the smoothing processing.

15. The electronic device according to claim 9, wherein the confidence of the first heart rate meeting the preset confidence condition comprises:

the confidence of the first heart rate being greater than a confidence threshold.

16. The electronic device according to claim 9, the operations further comprising:

storing a plurality of heart rate values whose confidences meet the preset confidence condition;

generating a heart rate curve based on the plurality of heart rate values; and displaying the heart rate curve.

17. A non-transitory computer-readable storage medium, storing a computer program that, when executed by an electronic device, causes the electronic device to perform operations including:

determining that a wearer of the electronic device is a living body;

obtaining a first photoplethysmograph (PPG) signal;

determining a first heart rate and a confidence of the first heart rate according to the first PPG signal, wherein the confidence of the first heart rate is determined based on weight coefficients of M harmonic signals, wherein the M harmonic signals are determined according to the first PPG signal within a preset time, and M is an integer greater than or equal to 2, the determining the first heart rate and the confidence of the first heart rate comprising:

calculating a corresponding weight coefficient of each of the M harmonic signals;

determining a corresponding confidence of the corresponding weight coefficient of each of the M harmonic signals to obtain M confidences; and using a highest confidence among the M confidences as the confidence of the first heart rate, wherein the calculating the corresponding weight coefficient of each of the M harmonic signals comprises:

calculating a relative error of each harmonic signal relative to an ideal signal, wherein the ideal signal is obtained by multiplying a previous signal at a previous moment of a current moment by a phase at a next moment, and dividing the relative error of each harmonic signal by a sum of relative errors of the M harmonic signals to obtain the corresponding weight coefficient of each of the M harmonic signals;

outputting the first heart rate based on the confidence of the first heart rate meeting a preset confidence condition; and displaying the first heart rate.

18. The non-transitory computer-readable storage medium according to claim 17, the operations further comprising:

displaying a second heart rate based on the confidence of the first heart rate not meeting the preset confidence condition, wherein the second heart rate is a heart rate that meets the preset confidence condition last time.

19. The non-transitory computer-readable storage medium according to claim 17, the determining the first heart rate and the confidence of the first heart rate further comprising:

performing smoothing processing on the first PPG signal to obtain a smoothed PPG signal after the smoothing processing;

performing band-pass filtering on the smoothed PPG signal after the smoothing processing to obtain a second PPG signal, wherein the second PPG signal is in a target frequency band range;

performing Hilbert transform on the second PPG signal to obtain an analytic signal of the second PPG signal, wherein a derivative of a phase of the analytic signal is an instantaneous frequency;

performing notch processing on the analytic signal to obtain a third PPG signal, wherein the third PPG signal does not comprise a motion interference signal; and filtering the third PPG signal through M filters to obtain the M harmonic signals.

* * * * *